(12) United States Patent
Winstead et al.

(10) Patent No.: US 7,989,065 B2
(45) Date of Patent: Aug. 2, 2011

(54) MAGNETICALLY-RESPONSIVE MICROPARTICLES WITH IMPROVED RESPONSE TIMES

(75) Inventors: J Winstead, Indianapolis, IN (US); William L. Grimm, Indianapolis, IN (US)

(73) Assignee: Seradyn, Inc., Indianapolis, IN (US)

( * ) Notice: Subject to any disclaimer, the term of this patent is extended or adjusted under 35 U.S.C. 154(b) by 465 days.

(21) Appl. No.: 11/436,680

(22) Filed: May 18, 2006

(65) Prior Publication Data
US 2006/0269751 A1   Nov. 30, 2006

Related U.S. Application Data

(60) Provisional application No. 60/683,051, filed on May 20, 2005.

(51) Int. Cl.
*B32B 5/16* (2006.01)
(52) U.S. Cl. ........ 428/403; 428/404; 428/405; 428/406; 428/407; 427/127; 427/128; 427/129; 427/130; 427/212
(58) Field of Classification Search .......... 428/403–407, 428/694 B; 427/127–131, 212
See application file for complete search history.

(56) References Cited

U.S. PATENT DOCUMENTS

| | | | |
|---|---|---|---|
| 4,177,253 A | 12/1979 | Davies et al. | |
| 4,230,685 A | 10/1980 | Senyei et al. | |
| 4,329,241 A | 5/1982 | Massart | |
| 4,695,392 A | 9/1987 | Whitehead et al. | |
| 4,770,183 A | 9/1988 | Groman et al. | |
| 4,810,401 A * | 3/1989 | Mair et al. | 252/62.56 |
| 5,069,216 A | 12/1991 | Groman et al. | |
| 5,091,206 A * | 2/1992 | Wang et al. | 427/2.18 |
| 5,648,124 A * | 7/1997 | Sutor | 427/475 |
| 6,133,047 A * | 10/2000 | Elaissari et al. | 436/526 |
| 6,682,660 B2 * | 1/2004 | Sucholeiki et al. | 252/62.54 |

FOREIGN PATENT DOCUMENTS

| | | | |
|---|---|---|---|
| WO | WO89/04373 | * | 5/1989 |
| WO | WO 89/04373 | | 5/1989 |
| WO | WO 99/35500 | | 7/1999 |

OTHER PUBLICATIONS

European Search Report from European Patent Application No. 06784450.6, dated Mar. 18, 2009 (copy attached).

* cited by examiner

*Primary Examiner* — Monique R Jackson
(74) *Attorney, Agent, or Firm* — Workman Nydegger

(57) ABSTRACT

Magnetically responsive particles can include two or more magnetically responsive layers ("MRL"). As such, the particles can have the following: a polymeric core; a first magnetically responsive layer ("MRL") on the core; a first polymeric layer bound to the first MRL; a second MRL layer bound to the first polymeric layer; and a second polymeric layer bound to the second MRL. The particles can have a faster magnetic response time compared to a similar particle having only a single MRL, which can be at least 25% faster. Also, the particle can have a magnetic squareness of less than about 0.1. Preferably, the particle can have negligible residual magnetism after being exposed to a magnetic field sufficient for the particle to respond thereto. Further, the particle can be colloidally stable in water at concentrations from about 0.1 to 10 grams of particle per 100 milliliters of water.

22 Claims, 7 Drawing Sheets

US 7,989,065 B2

MAGNETICALLY-RESPONSIVE MICROPARTICLES WITH IMPROVED RESPONSE TIMES

CROSS-REFERENCE TO RELATED APPLICATIONS

This United States Patent Application claims benefit of U.S. Provisional Application having Ser. No. 60/683,051, entitled, "MAGNETICALLY-RESPONSIVE MICROPARTICLES WITH IMPROVED RESPONSE TIMES," which was filed on May 20, 2005, with Winstead et al. as inventors, which is incorporated herein by reference.

FIELD OF THE INVENTION

The present invention relates to magnetically responsive particles ("MRP"), their preparation, and their use in applications for separating substances bound to the MRP from samples. Such applications can include immunoassays, the separation of cells, and use in magnetic resonance imaging. More particularly, the present invention relates to micro-scale MRPs that include multiple layers of magnetically responsive materials ("MRM") that have improved response times and stability.

BACKGROUND OF THE INVENTION

Magnetically responsive particles ("MRP") can be useful in biological techniques requiring the separation of a target substance from a sample. As such, the MRP can include moieties that interact or bind with the target substance so that it can be separated from the sample. Typically, MRPs have micro-scale dimensions, and can be useful in immunoassays, for the separation of cells from cell cultures or other samples, and as magnetic resonance imaging agents. Various uses of MRPs have been described in U.S. Pat. Nos. 4,177,253, 4,230,685, 4,329,241, 4,695,392, 4,770,183, 5,069,216, 5,091,206, 5,648,124, 6,133,047, and 6,682,660, which are incorporated herein by reference.

In some instances, it may be preferable for the MRPs to have dimensions (e.g., diameters for spheres), which cover the range of the visible light spectrum so as to facilitate heterogeneous and homogeneous immunoassay methods. However, it can be difficult to prepare a single particle size and associated particle size distribution that can be useful for a broad range of experimental procedures. For example, particles that are useful in automated experimental protocols may not be useful in experiments run by hand.

In some instances, it can be preferable that the MRPs have negligible residual magnetism. Unfortunately, some MRPs having large amounts of MRMs have shown considerable residual magnetism due to the characteristics of the magnetic materials. Such residual magnetism can cause clumping in the absence of a magnetic field in a manner resulting in the magnetic particles being caused to fall out of Brownian motion and quickly settle out of suspension. Further, the large size of magnetite particles that have been used in some MRPs can limit the overall size of the MRP.

Additional problems that can be encountered with MRPs can include the stability and response time of the particle. Usually, increases in particle stability can be offset by longer and unfavorable response times. In part, this is because an increase in materials that are not magnetically responsive imparts particle stability, and addition of such materials can significantly alter the behavior of the particles in solution and/or under a magnetic field. On the other hand, increases in materials that are responsive to magnetic fields can lead to particle instability. It is thought that this may inherently result from the magnetically responsive materials ("MRM") having adverse reactions with each other as the amount or concentration increases. Also, increasing the amount or concentration of MRMs on a core particle may result in ineffective agglutination leading to instability at the core-MRM boundary, which significantly decreases the lifespan of the particle.

Therefore, it would be advantageous to have an improved MRP that can be used in a broad range of experimental protocols such as in automated and/or manual immunoassays, separation of cells, and magnetic resonance imaging. Additionally, it would be beneficial to have micro-scale MRPs that have improved response times and stability.

SUMMARY OF THE INVENTION

Generally, the present invention can include magnetically responsive particles ("MRP") that have multiple layers of magnetically responsive materials ("MRM"). Accordingly, an exemplary MRP can include the following: a polymeric core; a first magnetically responsive layer ("MRL") on the core, said first MRL comprising a plurality of MRMs agglutinated to the core; a first polymeric layer encapsulating the first MRL, said first polymeric layer being formed by cross-linking a first monomer having a first reactive group and a second monomer having a reactive group; a second MRL layer on the first polymeric layer, said second MRL comprising a plurality of MRMs, a portion of said MRMs being bound to the first polymeric layer; and a second polymeric layer encapsulating the second MRL said second polymeric layer formed by cross-linking a third monomer having a third reactive group and a fourth monomer having a fourth reactive group. The monomers can be separate monomers or included within a polymer.

Additionally, an MRP can have at least one additional MRL and at least one additional polymeric layer, wherein the additional MRLs alternate with the additional polymeric layers. Also, the MRP can include a heterocoagulant that is coagulated with the MRMs of the first MRL so as to facilitate binding with the core, or coagulated with the MRM of the second MRL so as to facilitate binding with the first polymeric layer. Further, the MRP can include a dispersant present on at least one of the first magnetically responsive layer or second magnetically responsive layer. The dispersant is at least one of the following: cross-linked together; cross-linked with a heterocoagulant to form a polymeric layer; or cross-linked together and cross-linked with the heterocoagulant. Also, any of the polymeric layers can be comprised of an acidic monomer, basic monomer, hydrophobic neutral monomer, polar monomer, or a polymer thereof.

In one embodiment, a MRP can include the following: a polymeric core; a first MRL on the core, said first MRL comprising a plurality of MRMs; a first heterocoagulant intermingled with the MRM; a dispersant covering a least a portion of the first MRL and cross-linked with the heterocoagulant to form a first polymeric layer; a second MRL on the first polymeric layer, said second MRL comprising a plurality of magnetically responsive materials, a portion of said magnetically responsive materials being bound to the first polymeric layer; a second heterocoagulant intermingled with the MRMs of the second MRL; and a second dispersant covering the second MRL and cross-linked with the second hetero coagulant to form a second polymeric layer.

Additionally, any of the MRPs described herein can have various properties. As such, the particle can have a faster magnetic response time compared to the particle without the second magnetically responsive layer and the second polymeric layer. Preferably, the magnetic response time is at least 25% faster. Also, the MRP can have a magnetic squareness of less than about 0.1, and preferably less than about or equal to 0.05. Most preferably, the MRP can have negligible residual magnetism after being exposed to a magnetic field sufficient for the particle to respond thereto. Further, the MRP can be colloidally stable in water at concentrations from about 0.1 to 10 grams of particle per 100 milliliters of water. Furthermore, the MRP can have only two magnetically responsive layers, or it can have more than two magnetically responsive layers.

In one embodiment, the present invention can include a method of preparing an MRP having multiple MRLs. Such a method can include the following: preparing a first aqueous dispersion comprising a core and an MRM in a manner such that the MRM agglutinates to the core to form a first magnetically responsive layer; adding at least one of a heterocoagulant or a dispersant to the first MRL on the core so as to form a second aqueous dispersion therewith; encapsulating the first MRL having the heterocoagulant or dispersant to form a first polymeric layer; adding additional MRM to the first polymeric layer so as to form a second MRL on the first polymeric layer, wherein the MRM bonds with the first polymeric layer; or second heterocoagulant to the second adding at least one of a second dispersant and encapsulating the second MRL with a second polymeric layer. Optionally, the heterocoagulant and dispersant can be cross-linked together by forming a cross-linked MRL to form the polymeric layers. In another option, the first polymeric layer or second polymeric layer can be formed by adding a polymerizable monomer or polymer and a polymerization initiator so as to induce polymerization of the monomer or polymer. In yet another option, the magnetically responsive material is provided in a ferrofluid or a superferrofluid.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawing. It is appreciated that this drawing depicts only a typical embodiment of the invention and is therefore not to be considered limiting of its scope.

DETAILED DESCRIPTION OF THE PREFERRED EMBODIMENTS

Figure 1:
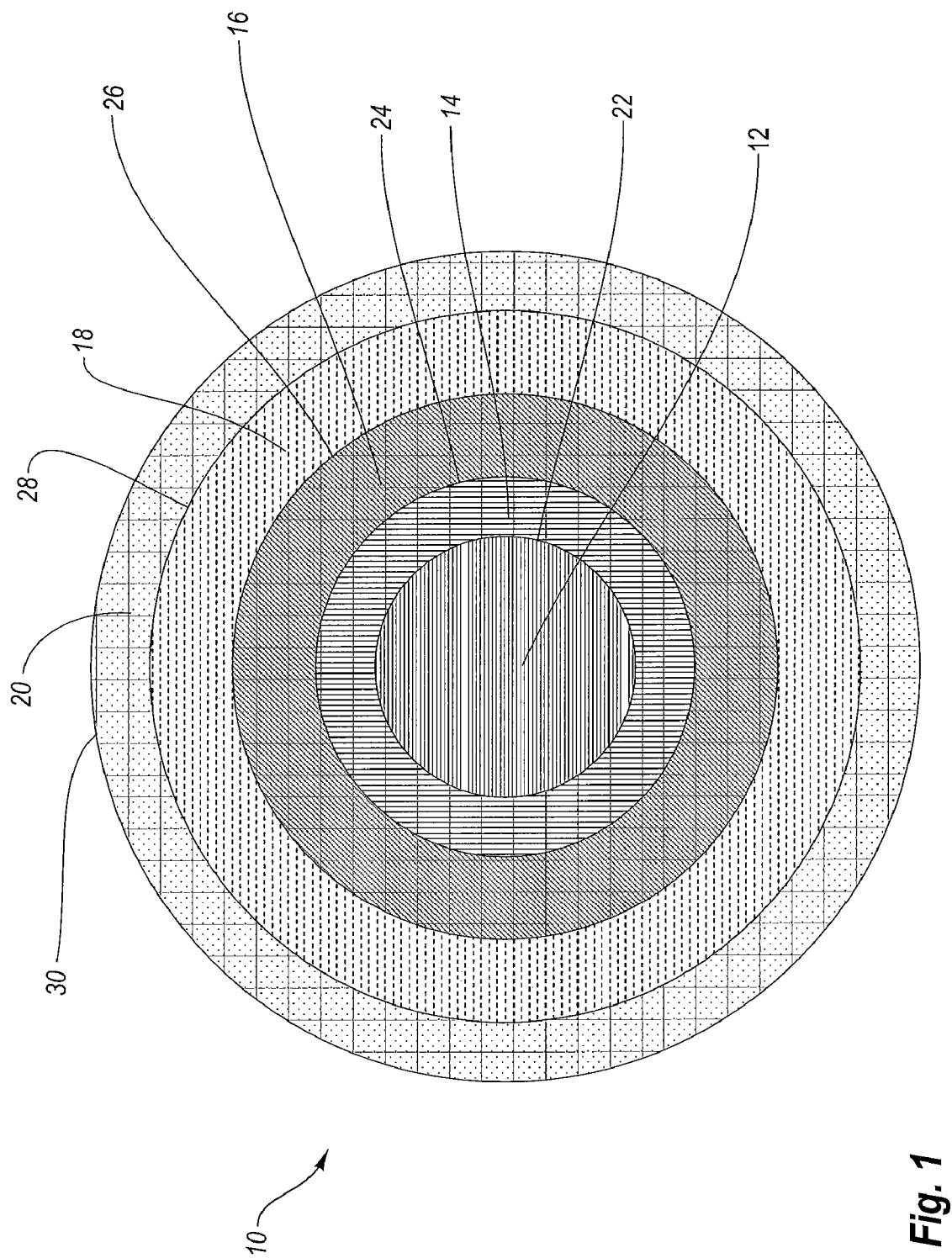
FIG. 1 is a schematic representation illustrating a cross-sectional view of an exemplary MRP having multiple MRLs.
Figure 2:
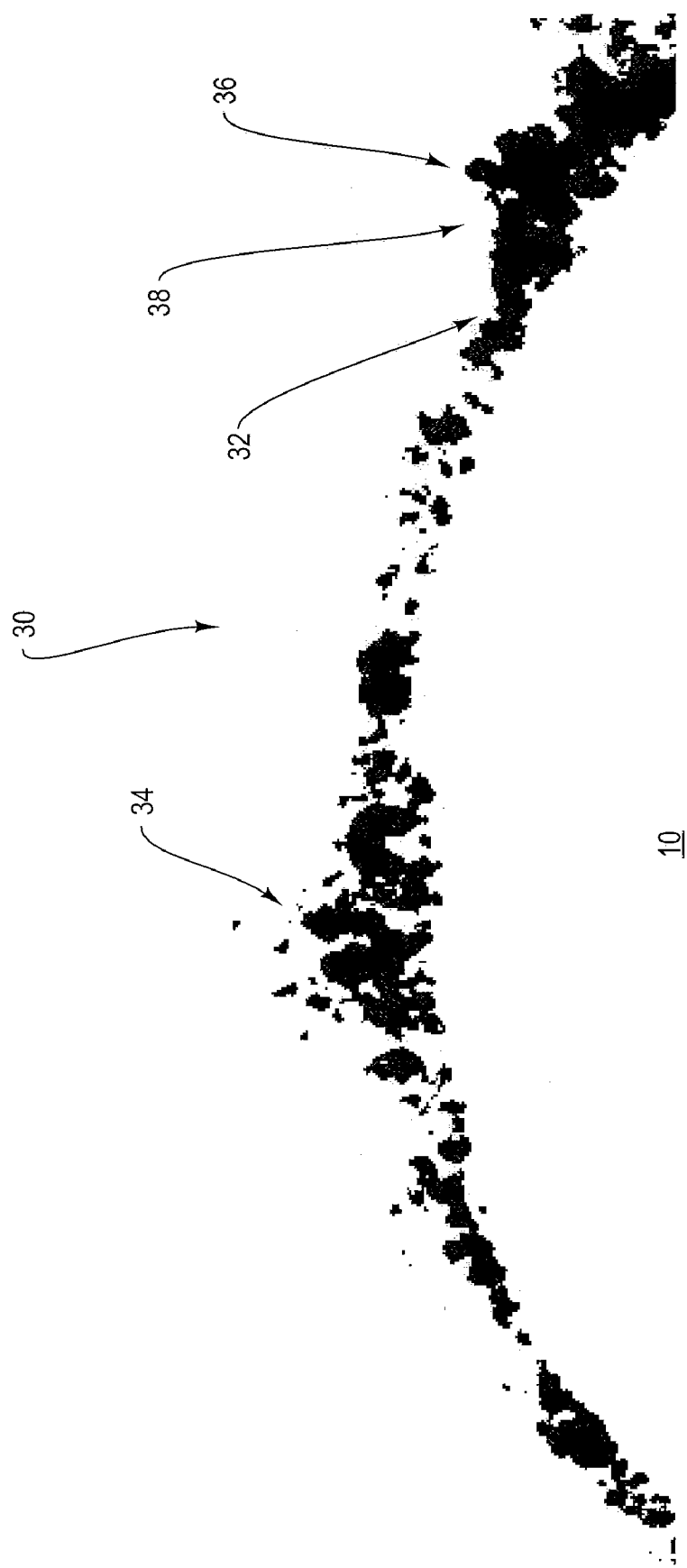
FIG. 2 is a schematic representation of an external surface of an exemplary MRP.

Generally, the present invention can include a magnetically responsive particle ("MRP") for use in a broad range of experimental protocols such as in automated and/or manual RP from samples, such as in immunoassays, the separation of cells, and as magnetic resonance imaging agents. The MRP can include a plurality of magnetically responsive layers ("MRL") radially disposed from an internal core. The MRP can include at least two or more of such MRLs, wherein the MRLs can have the same or different compositions. Also, each MRL can be comprised of magnetically responsive materials ("MRM") that are agglutinated together and to the underlying core or layer. The MRLs can be configured in a manner that results in the MRP responding to magnetic fields without having any or without significant residual magnetism.

Additionally, the MRP can include polymeric layers radially disposed outward from each MRL. The polymeric layers can have various configurations, and can have various functions in relation to the MRLs. Accordingly, the polymeric layer can be useful for sealing a first MRL from a radially-adjacent MRL, and to protect the outermost MRL from environmental conditions, contaminants, and components within a sample.

I. Introduction

It has now been discovered that the combination of multiple layers of MRMs separated by polymeric layers can improve the performance of MRPs. Additionally, the combination of a plurality of MRLs and a plurality of polymeric layers can be adapted for particles having micro-scale dimensions. Further, the MRPs having multiple MRLs can have improved response times compared to other magnetic particles. Moreover, the MRPs having multiple MRLs can have improved stability so that the particles retain their stricture and characteristics throughout a single experiment and have a longer lifespan compared to other magnetic particles.

The MRPs in accordance with the present invention can have widely varied dimensions. Also, the MRPs can have dimensions (e.g., diameter) that are varied within wide limits that cover the wavelength range of the visible light spectrum. Such MRPs can be useful in a variety of homogeneous and heterogeneous experimental procedures in the realm of immunodiagnostics. Also, the MRM can be configured with dimensions that have negligible settling rates, which are ideally suited for oligonucleotide synthesis, biological separations, immunoassays, and the like.

Also, it can be beneficial for the MRP to have various settling weights that can affect the settling rates. The settling weights and associated settling rates can be altered by changing the density and/or size of the core, MRLs, polymer layers, or overall density and/or size of the particle.

Moreover, the MRPs can be configured to have wide or narrow differences in dimensions, which can be characterized by polydispersity factors $\mu/\mu^2$ (i.e., $mu^2/gamma^2$). Preferably, the polydispersity factors can range from about 0.01 to about 0.500. Also, in some instances it may be favorable for the MRPs to have a substantially monodisperse polydispersity.

The MRPs can also be configured to have different external surface characteristics depending on end uses. As such, the external surface can be modified and adapted to be useful in a variety of applications. This can include modifying the surface chemistry so that the surface charge can be neutral, positive, or negative. Also, amphoteric surfaces can also be prepared. Additionally, the surface can be modified so that it can be hydrophobic, hydrophilic, amphiphilic, lipophilic, and the like. Moreover, the surface chemistry can be modified so as to be compatible with receptors, antigens, ligands, antibodies, and the like that are commonly applied to well-known particles that are similar to those described herein (e.g., see incorporated references). This can provide MRPs that are ideally suited for PCR, oligonucleotide synthesis, biological separations, immunoassays, and the like. Moreover, the MRPs can be configured to have surface characteristics that are not adverse to experimental protocols. For example, the MRPs can be configured to activate or turn over a peroxidase substrate system in a PCR assay so that an assay does not give false positive results.

Additionally, a MRP can be configured to have variations in surface area. That is, the particles can be prepared to have substantially smooth surfaces to provide smaller surface areas, or they can be prepared to have significant roughness to provide larger surface areas. Also, an MRP can have any type of surface area between smoothness or roughness. An MRP can have an increased surface area by having a significant amount of recesses, protrusions, overhangs, and/or undercuts. Increasing the amount and/or size of such surface characteristics can increase the surface area. For example, small surface areas can be useful for magnetic resonance imaging agents or when a small number of substituents are coupled to the MRP, and large surface areas can be useful for increasing the adsorption potential of the particle or when a large number of substituents are coupled to the MRP.

Additionally, an embodiment of the present invention can include novel methods for producing MRPs having a plurality of MRLs. This can include methods of producing MRPs having varied MRM content and negligible residual magnetism. As such, the methods can include varying the amount of the MRM within each MRL. Each MRP can have significantly more electromagnetic units ("EMU") per weight of the particle. This can be accomplished by increasing the amount of MRM in each MRL. Also, this can be accomplished by decreasing the weight of the non-MRM materials within each MRP.

Also, the method of producing MRPs can utilize binders in order to improve agglutination of the MRM to the core or underlying layer, wherein such binders can favorably interact with the core or radially-adjacent polymeric layers. As such, the MRM can be agglutinated or heterocoagulated on a core (e.g., polystyrene spheroid), overcoated or co-agglutinated with a binder (e.g., polyethyleneimine or PEI), and crosslinked with a coating polymer layer (e.g., polyacrylate, polymethacrylate, and the like). This process can be followed by repeating the cycle of adding additional layers of MRMs, binder, and polymers.

II. Magnetically Responsive Particles

Generally, an MRP in accordance with the present invention can include a core and a plurality of layers of MRM and a plurality of polymeric layers. FIG. 1 illustrates such an MRP 10. The MRP 10 can be comprised of a core 12 that can be prepared from various types of materials, such as polymers, ceramics, and metals. The core 12 can be surrounded by a first MRL 14, which can include a plurality of agglutinated nanoparticles or microparticles formed from an MRM. The first MRL 14 can be surrounded by a first polymeric layer 16, which can comprise a single type of polymer or a combination of different types of polymers. The first polymeric layer 16 can be surrounded by a second MRL 18, which can be configured similarly or differently from the first MRL 14. The second MRL 18 can be surrounded by a second polymeric layer 20, which can be configured similarly or differently from the first polymeric layer 16. Additional MRLs and polymeric layers can be included in an MRP 10 as desired.

Additionally, a first interface 22 can be disposed between the core 12 and the first MRL 14. The first interface 22 can include various types of chemical and/or physical bonds (e.g., covalent, ionic, mechanical, etc.) couplings, combinations thereof, or the like. Usually, the first interface 22 is an interfacial region that comprises aspects of the core 12 and first MRL 14 and can have characteristics arising from agglutination of the MRM with the material of the core. Also, bonding agents can be used to enhance the first interface 22. The first interface 22 can be substantially smooth or substantially rough depending on the characteristics of the surface of the core 12 and whether or not spaces or voids are formed between the core 12 and the first MRL 14.

The MRP 10 can also include a second interface 24 can be disposed between the first MRL 14 and the first polymeric layer 16. The second interface 24 can include various types of chemical and/or physical bonds (e.g., covalent, ionic, mechanical, etc.), couplings, combinations thereof, or the like. Usually, the second interface 24 is an interfacial region that comprises aspects of the first MRL 14 and first polymeric layer 16 and can have characteristics arising from the agglutinated MRM in the first MRL 14, heterocoagulants or binder bound to the MRM, cross-linkers, and the first polymeric layer 16. The second interface 24 can be substantially smooth or substantially rough depending on the characteristics of the surface of the first MRL 14 and whether or not spaces or voids are formed between the first MRL 14 and the first polymeric layer 16.

Additionally, the MRP 10 can include a third interface 26 between the first polymeric layer 16 and the second MRL 18. The third interface 26 can be ionic with the second MRL 18 ionically associating with the first polymeric layer 16. That is, the second MRL 18 can be over-coated onto the first polymeric layer 16 to form ionic bonds therewith. Also, the MRP 10 can include a fourth interface 28 between the second MRL 18 and the second polymeric layer 20. The fourth interface 28 can be substantially similar to the second interface 24 or third interface 26.

The MRP 10 can also include an external surface 30. The external surface 30 can be configured to have various surface characteristics and variations in surface area. That is, the MRP 10 can be prepared to have substantially smooth surfaces to provide smaller surface areas, or they can be prepared to have significant roughness to provide larger surface areas. Also, the MRP 10 can have any type of surface area between smoothness or roughness, and can be substantially similar to the first polymeric layer 16 aspect of the third interface 26.

FIG. 2 is a schematic diagram of the external surface 30 of an exemplary MRP 10. As shown, the external surface 30 can have an increased surface area by having a significant amount of recesses 32, protrusions 34, overhangs 36, and/or undercuts 38. Increasing the amount and/or size of such surface characteristics can increase the surface area. The schematic diagram of the external surface 30 can also represent an embodiment of any of the interfaces described herein.

Additionally, the MRP can include a plurality of MRLs and a plurality of polymeric layers. This can include such plurality of MRLs and plurality of polymeric layers alternating as described above. As such, an MRP can include a core with a plurality of MRLs extending outwardly-radially therefrom with at least one polymeric layer between each sequential MRL. Also, the MRLs can include polymeric materials that aid in binding the polymeric layers.

For example, the core 12, first MRL 14, and first polymeric layer 16 can be substantially similar to the particles described in the incorporated reference U.S. Pat. No. 5,648,124, which describes examples of the core, the first MRL, and the first polymeric coating. Additionally, methods for preparing the particles are described therein.

An MRP in accordance with the present invention can have various discrete compositions and configurations to provide improved functionality. As such, examples of such compositions, individual materials, and configurations of such materials are provided in more detail below.

1. Core

The core of an MRP in accordance with the present invention is preferably at least substantially spherical; however, other shapes may be used. The core can be a particle that is made of a variety of materials including silica, alumina, albumin, polymers, ceramics, metals, and the like. Accordingly, materials that are well known for preparing nano-scale to micro-scale particles can be used. However, the core particles according to the invention are preferably non-magnetic and/or non-magnetically responsive.

For example, core particles are preferably prepared from a polymer. Such polymers can include those made from styrene, methylstyrene, ethylstyrene, and homologs thereof, and methyl acrylate, ethyl acrylate, methyl methacrylate, ethyl methacrylate, and homologs thereof. Also, the core particles may be prepared with or without the addition of ionogenic comonomers such as 2-acrylamido-2-methyl propanesulfonic acid ("AMPS"), sodium alkyl sulfonate, sodium methallyl sulfonate, vinyl sulfonate, sodium p-styrene sulfonate, potassium p-styrene sulfonate, acrylic acid, fumaric acid, maleic acid, methacrylic acid, itaconic acid, and salts thereof; aminoethylmethacylate, dimethylaminoethyl methacrylate, t-butylaminoethyl methacrylate, pyrrole, N-vinyl carbazole, vinylpyridines, and salts thereof. Of course a mixture of the monomers and optional comonomers may be used to produce polymeric cores having the desired size and surface charge characteristics. Particularly preferred polymeric cores are those of polymethylmethacrylate, carboxylate-modified polymethylmethacrylate, polystyrene, and carboxylate-modified polystyrene.

The surface of the core particles may be prepared with positive or negative charge. For example, if the core is made with polyacrylic acid, the acid groups can impart a negative charge to the surface of the core. If the core is made with aminoethylmethacrylate, the amino groups can impart a positive charge to the surface of the core. For polymers having no active hydrogens (e.g., polystyrene), surface charge may be provided by the initiator used to produce the polymer. For example, styrene monomer polymerized in the presence of a persulfate initiator will provide a polystyrene core having a negative surface charge while polystyrene polymerized with 2,2'-azobis (2-methylpropionamidine)dihydrochloride initiator will provide polystyrene with a positive charge. Examples of initiators which provide a negative charge are persulfate, 4,4'-azobis (4-cyanovaleric acid) and potassium peroxydiphosphate. Any initiator that provides a negative surface charge may be used. Any initiator which provides a positive charge may be used. The surface charge of the core particle can be measured by conductometric titration and is generally from about 0.005 to about 1.5 milliequivalents per gram ("meq/g") of core particle, preferably about 0.01 to about 1.0, and most preferably about 0.02 to about 0.8 meq/g of core particle.

Also, the core can be any size from 0.05 to 10.0 microns in size, more preferably from 0.25 to 5.0 microns, and most preferably from 0.1 to 1.0 microns in size. Additionally, it can be preferable for the core particles to have substantial uniformity in size. That is, it is preferable for the core particles to be substantially monodisperse (i.e., have polydispersities of $\leq 0.1 \ \mu^2/\gamma^2$).

Polymeric core particles according to the invention may be obtained by any technique known in the art, with emulsion polymerization, seeded emulsion polymerization, and dispersion polymerization being particularly preferred. The polymeric core particles may be made with or without a cross-linking agent.

Additionally, the core can be treated with fumaric acid or other acid to provide a low acid content. Preferably, the acid content of the core is about 0.02 to 0.80 meq/g of core material. As such, the core can have carboxylic acid groups at the surface that provide one or two acid groups per monomer unit that is treated.

2. Magnetically Responsive Material

In order to respond to magnetic fields, the MRP of the present invention can include an MRM. The MRM can be responsive to magnetic fields, but it preferred that the MRP does not retain magnetism. As such, it can be preferred for the MRM to be a superparamagnetic material. For example, the superparamagnetic material can be magnetite. The superparamagnetic material can be prepared by the addition of base to an aqueous mixture of ferrous and ferric sulfate or chloride. Also, it can be preferred to a use a mixture of $FeCl_3$ and $FeCl_2$. For example, the molar ratio of the trivalent to the divalent metal salt can be varied from about 1.0 to about 3.0, more preferably from about 1.5 to about 2.5, and most preferably from about 1.8 to about 2.2. These ranges can be useful to obtain the desired size and magnetic characteristics of the superparamagnetic material. Additionally, divalent transitional metal salts such as cobalt, manganese, nickel, zinc salts and their mixtures, may be substituted for some or all of the ferrous salt. Other superparamagnetic particles according to the present invention, and methods for their preparation, are described in U.S. Pat. No. 4,810,401, incorporated herein by reference.

Any suitable base can be added to the aqueous mixture of the metal material. Preferably the base is ammonium hydroxide when the metal is a divalent and/or trivalent iron salt.

The MRM including the superparamagnetic magnetite can be peptized or finely divided to subdomain size such that no net magnetic dipole remains in the individual grains of magnetite. Typically, the size of the peptized grains varies from 1 to 200 nm as measured by quasielastic light scattering. However, it can be preferable that the grain size ranges from about 5 to about 150 nm, more preferably from about 10 to about 120 nm, and most preferably from about 30 to about 70 nm. For example, peptized grains of 10 to 120 nm are particularly useful in the invention.

Peptizing may by accomplished by treating coarse aggregates of magnetite with acid or base until the desired size is obtained. Further, a net positive or negative surface charge can be imparted to grains or superparamagnetic magnetite by the acid or base. Since magnetite is amphoteric, treatment with acid produces a positively charged superparamagnetic magnetite, and treatment with base produces a negatively charged superparamagnetic magnetite.

The peptized grains can be used to prepare ferrofluids, which are used to agglutinate the superparamagnetic grains to the core particle. The ferrofluids or superferrofluids may be used in the present invention as magnetically responsive material to coat the above-described cores. A ferrofluid can be described as having a colloidal dispersion comprising a stable concentration of small magnetic grains dispersed in a continuous liquid phase. As described in more detail below, the magnetic grains can include $Fe_3O_4$, $Fe_2O_3$, and Fe. It is preferred that the ferrofluids be configured to have super-paramagnetic properties. Also, it is preferred that the ferrofluids provide a magnetization curve without a hysteresis, wherein no hysteresis is an indication the ferrofluids or MRP prepared therefrom do not have any residual magnetism after being exposed to a magnetic field.

The superferrofluids can include mixed $Co_yMn_wZn_xFe_yO_4$ and $Ni_yMn_wZn_xFe_yO_4$ and others described in U.S. Pat. No. 4,810,401, which is incorporated herein by reference. This can include the superferrofluids having $Co_{0.1}Mn_{0.2}Zn_{0.2}Fe_{2.5}O_{3.7}$ and $Ni_{0.1}Mn_{0.2}Zn_{0.2}Fe_{2.5}O_{3.9}$, which are particularly preferred. Further, particularly preferred-superferrofluids can have magnetic saturations of up to 40% greater than magnetite (e.g., $Fe_3O_4$) including all values and all ranges therebetween.

The magnetic saturation of a MRM can be process dependent, and tailored thereby depending on the process. For example, a magnetite ferrofluid can have a saturation of about 73.7 EMU/g. If the ferrofluid materials described above are used in the same process, the saturation can be modulated to be from about 5% to about 40% greater depending on the specific material and process.

3. Heterocoagulant

The MRP of the present invention can utilize a heterocoagulant or binder in order to enhance the agglutination of the MRM to the core. The heterocoagulant or binding agent can include the following, alone or in combination: ammonium or alkali metal salts of sulfate and phosphate; free radical generating ammonium or alkali metal salts of peroxydisulfate, peroxydiphosphate, and 4,4-azobis (4-cyanovaleric acid); ammonium or alkali metal salts of oxalic acid, malonic acid, succinic acid, glutaric acid, and the like; polymerizable ammonium or alkali metal salts of fumaric acid, maleic acid, and itaconic acid; ammonium or alkali metal salts of alkyl sulfonates such as dihexylsulfosuccinate and dioctylsulfosuccinate; polymerizable ammonium or alkali metal salts of alpha olefin sulfonates, alkyl allyl sulfosuccinates, and allyl ether sulfonate, the latter three surfactants having 6 to 30 carbon atoms; ammonia, alkylamines, and polyalkylamines such as polyethylenimine; and polyacrylic acid and water soluble copolymers and salts thereof, polymethacrylic acid and water soluble copolymers and salts thereof, polystyrenesulfonic acid and water soluble copolymers and salts thereof, polyvinylsulfonic acid and water soluble copolymers and salts thereof, styrene/maleic acid copolymers, half esters, and salts thereof, vinyl methyl ether/maleic acid copolymers, half esters, and salts thereof, all with weight average molecular weights of 1,000 to 100,000 daltons. The ammonium or alkali metal sulfates and phosphates may be generated in situ by the thermal decomposition of homogeneous precipitating agents such as dimethyl sulfate, sulfamic acid, or trimethyl phosphate. Also, ammonia may be generated in situ by the thermal decomposition of urea. The heterocoagulants can be solid or liquid at room temperature and are generally used in amounts of from about 0.01 to about 0.20 grams per gram of core particles being coated with the MRM. Preferred heterocoagulants can include ammonium sulfate, sodium dioctylsulfosuccinate, polyacrylic acid, polymethacrylic acid, and the like.

4. Dispersant

The MRP of the present invention can utilize a dispersant in order to enhance the agglutination of the MRM to the core. The dispersant can be used in addition to or in place of the heterocoagulants or binders. Exemplary dispersants are preferably polymeric and can aid in preparing a suitable ferrofluid and for agglutinating the MRM to the core or underlying polymeric layer. Examples of suitable polymeric dispersants can include the following alone or in combination: polyacrylic acid and water soluble copolymers and salts thereof, polymethacrylic acid and water soluble copolymers and salts thereof, polystyrenesulfonic acid and water soluble copolymers and salts thereof, polyvinylsulfonic acid and water soluble copolymers and salts thereof, styrene/maleic acid copolymers, half esters, and salts thereof, vinyl methyl ether/maleic acid copolymers, half esters, and salts thereof; polyethyleneimine; combinations thereof, and the like. It is preferable for the dispersant to be polyacrylic acid, polyethyleneimine, polymethacrylic acid, and combinations thereof, which can act as heterocoagulants/dispersants.

Preferably, the average molecular weight of the dispersant is from 1,000 to 500,000 daltons, more preferably from about 2,500 to 250,000 daltons, and most preferably from about 5,000 to about 100,000 daltons. The polymeric dispersant can be added to the MRM as a solution at room temperature; however, powdered polymeric dispersant may be used as well. Additionally, preferred polymeric dispersants and their approximate molecular weight can include polyacrylic acid at from about 2,000 to about 100,000 daltons, and/or polymethacrylic acid at from about 2,000 to about 100,000 daltons.

The amount of polymeric dispersant added to the MRM can vary from about 0.01 to about 1 grams per gram of core particles, more preferably from about 0.005 to 0.20 grams per gram of core particles, and most preferably from about 0.075 to about 0.1 grams per gram of core particles.

5. Polymeric Layers and Coatings

The MRP of the present invention can utilize a polymeric layer or coating in order to enhance the retention of MRM to the core or to underlying layers. The polymeric layers or coating materials for the first and/or additional polymeric layers can include polymers or copolymers having acidic monomers, such as acrylic acid, methacrylic acid, fumaric acid, maleic acid, methacrylic acid, itaconic acid, vinyl acetic acid, 4-pentenoic acid, undecylenic acid, and salts thereof. Further, the polymeric layer or coating may include polymers or copolymers of basic monomers, such as aminoethylmethacrylate, dimethylaminoethyl methacrylate, t-butylaminoethyl methacrylate, pyrrole, N-vinyl carbazole, vinylpyridine, and salts thereof. Furthermore, the polymeric layer or coating may include polymers or copolymers of hydrophobic neutral monomers, such as methyl acrylate, ethyl acrylate, methyl methacrylate, ethyl methacrylate, styrene, methylstyrene, ethylstyrene, vinylnaphthalene, and homologs thereof. Additionally, polymers prepared from the foregoing monomers can be utilized in preparing polymeric layers and coatings.

The amount of monomer or polymer added in order to form an inner polymeric layer or outer polymeric coating can generally depend upon the amount of MRM agglutinated or heterocoagulated on the core particle and underlying polymeric layers. Generally, the amount used varies between 0.2 and 1.0 grams of monomer or polymer per gram of non-coated core particle.

Additionally, each polymeric layer or coating can have a high acid content, which aids in agglutinating the MRM thereto in order to prepare an MRL. The high acid content can be obtain by the acid groups on each monomer, such as 1 acid group per methacrylic acid group. As such, the first polymeric layer can have an acid content of about 0.1 to 0.8 meq/g of particle. The increase in acid content for the polymeric layers compared to the core can increase the rate of heterocoagulation of the MRM grains to acid groups on the polymer.

Accordingly, the MRPs in accordance with the present invention can be prepared to have diameters in the range of 0.1 to 12 microns, preferably 0.5 to 5.0 microns can be prepared with cores having diameters of about 0.05 to 10 microns and magnetite particles of approximately 30 to 70 nm. Thus, MRPs can be prepared to have a wide range of diameters, wherein useful overall diameters can range from about 0.05 to about 20 microns, more preferably from about 0.1 to about 15 microns, and most preferably from about 0.5 to about 10 microns.

6. External Functional Moieties

The external polymeric layer on an MRP prepared in accordance with the present invention can be modified to include a variety of functional moieties. The functional moieties can include antibodies, antibody fragments, antigens, haptens, ligands, receptors, and the like. These and other functional moieties can be coupled to the MRP by the carboxyl groups on the external polymeric coating. Accordingly, techniques well known in the art can be used to activate the carboxyl group in order to facilitate coupling via covalent bonding. However, it should be recognized that various other techniques can be used to provide the MRP with external functional moieties.

III. Preparing Magnetically Responsive Particles

An embodiment of the present invention includes processes for preparing MRPs having multiple MRLs. That is, the MRPs are prepared by sequentially applying MRLs outward from the inner core, wherein adjacent MRLs are separated by layers of polymeric materials. The sequential layers are deposited on the underlying core or layer by processes well known in the art and described herein.

The first MRL can be agglutinated to the core mainly through Van der Waals forces. However, the low acid content of the carboxylated polystyrene can impart a minimal amount of electrostatic interaction to drive the agglutination. Also, the cross-linking of the dispersant and/or polymeric layer can help retain the MRM to the core.

The MRPs having multiple MRLs can be prepared by a combination of adsorption through Van der Waals forces and electrostatic forces. The significant amount of acid groups present on each polymeric layer increases the propensity and rate at which the MRMs agglutinate to the polymer to form the next MRL. Also, heterocoagulation with a heterocoagulant and cross-linking the dispersant can aid in holding and retaining the MRL to the underlying polymeric layer. Further, the polymeric layer applied over the MRL can aid in holding that MRL to the particle and also provide for a surface having increased acid content for enhancing agglutination of MRMs thereto in order to form the next MRL. As such, using polymeric layers having high acid content to stabilize the underlying MRL also stabilizes the overlying MRL so that the overall stability of the MRP is increased. This increase in MRP stability by alternating layers of polymers with high acid contents and MRLs can increase the stability substantially more than previous particles having only one MRL.

Figure 3:
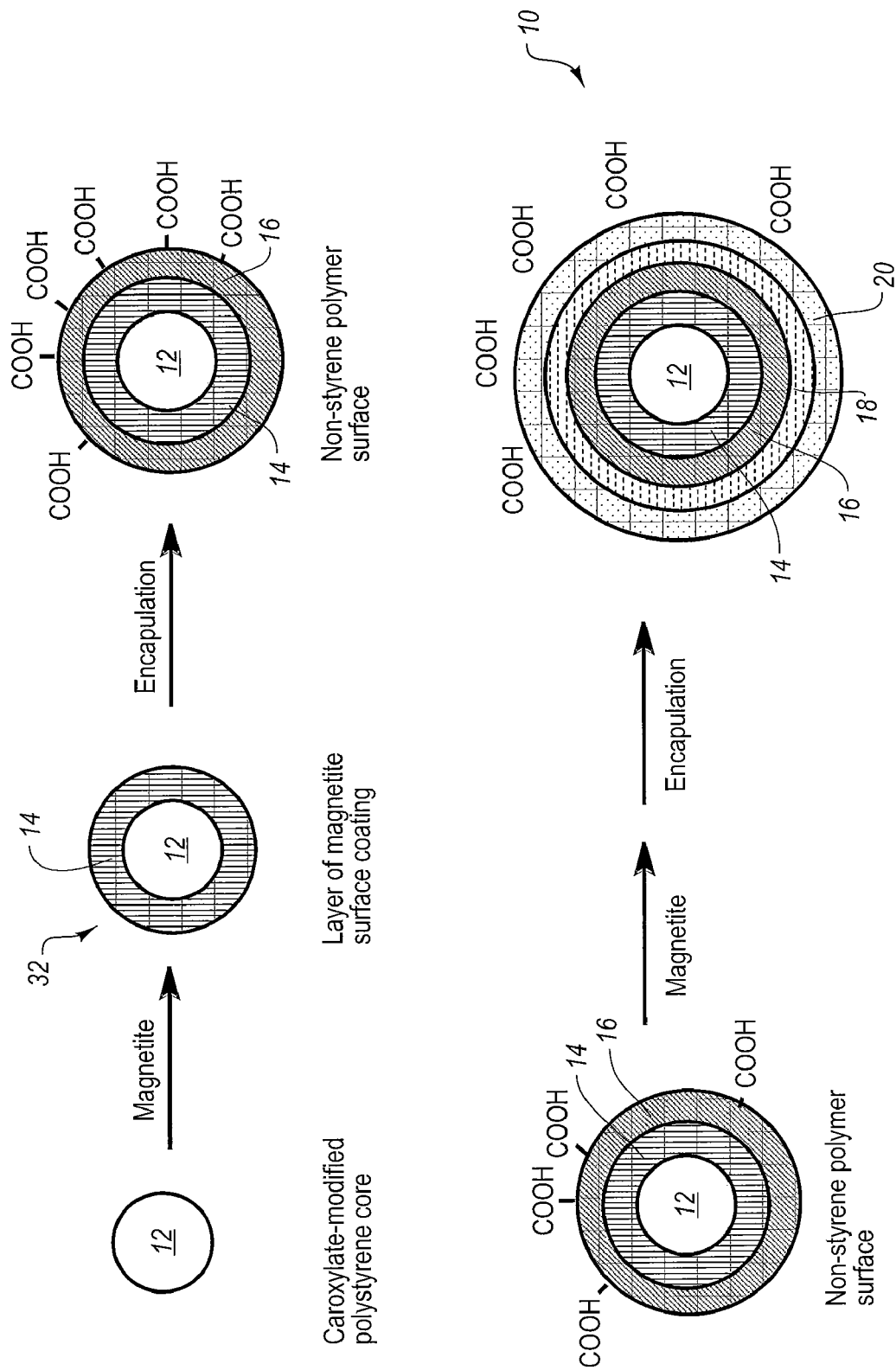
FIG. 3 is a schematic representation of a process for preparing the exemplary MRP of FIG. 1.

FIG. 3 is a schematic representation of a process for preparing an MRP 10 having a plurality of MRLs separated by a plurality of polymeric layers. As shown, a core 12 can be presented having carboxylate-modified polystyrene. The core 12 can then be coated with an MRL 14 of a MRM (e.g., magnetite). Usually, the MRL 14 can be formed by heterocoagulation by MRM by Van der Waals attraction with the core 12. The core/MRL particle 32 can then be encapsulated with a polymeric layer 16. The polymeric layer 16 can be characterized by being non-styrene and having a plurality of carboxyl groups, which can be exemplified by methacrylic acid groups that have 1 acid group per unit. The core/MRL 32 particle can be coated with a layer of magnetite to form another MRL 18. The outer MRL 18 can be encapsulated with another polymeric layer 20 so as to form the MRP 10. As shown, the MRP 10 has a plurality of carboxyl groups. Preferably, the outer MRL 18 has ionic associations with acid groups on both the polymeric layer 16 and/or the exterior polymer 20. Such ionic interactions increase the stability of the MRP 10.

Figure 4:
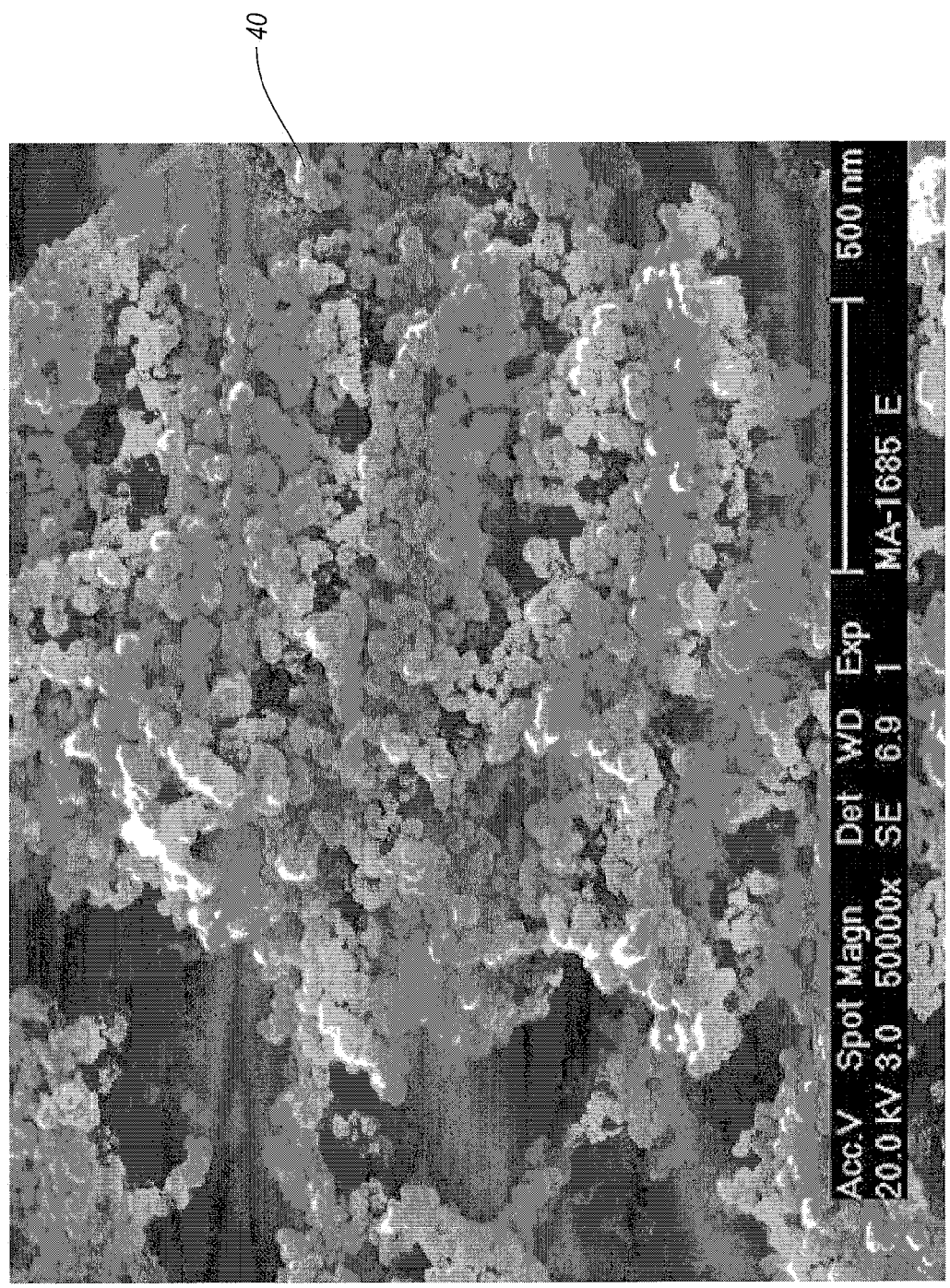
FIG. 4 is an SEM of an exemplary ferrofluid.

The MRP of the present invention can be prepared by sequentially heterocoagulating colloidally stable aqueous dispersions of magnetically responsive materials. Such solutions can be described as ferrofluids, super-ferrofluids, and the like, and can include materials, such as magnetite, that are paramagnetic or, preferably, superparamagnetic. An SEM of an exemplary ferrofluid can be seen in FIG. 4 where MRM grains 40 can be seen to agglutinate together. The ferrofluid including an MRM (e.g., magnetite) can be agglutinated onto the polymer surfaces of the core particles. The cores and the MRM (e.g, magnetite) can associate by Van der Waals forces and/or can be oppositely charged so as to heterocoagulate by electrostatic attraction; however, additional heterocoagulation can be achieved by addition of a heterocoagulant, binder, and/or dispersant.

After the desired degree of hetercoagulation of MRM to the core has been accomplished, a polymeric dispersant can be added. The polymeric dispersant can disperse the heterocoagulated MRM-coated cores so as to suspend them in solution where they can remain in Brownian motion in the absence of a magnetic field. If desired, the dispersed MRM-coated cores may be cross-linked with a suitable cross-linker, and/or further coated with one or more outer polymeric coatings.

Alternatively, a particle having the core/MRL/polymer can be obtained for preparing a multi-layered MRP. As such, an aqueous dispersion of oppositely charged MRM and core MRL/polymer particles can form a starting mixture for preparing MRPs with multiple MRLs. The opposing charges of the MRM and outer polymeric coating of the core/MRL/polymer particle can induce a charge-driven heterocoagulation process. The heterocoagulation process can proceed with or without the presence of an optional heterocoagulant, until the core particles are coated with approximately one layer of MRM, such as magnetite particles or grains, to form a MRP having a core/MRL/polymer/MRL configuration. In the presence of heterocoagulant, additional MRM can become coated and agglutinated onto the polymeric layer.

Heterocoagulation is preferably performed at room temperature, but is effective from about 0° to 100° C. The core particles, MRM, and optional heterocoagulant(s), binders, or dispersants may be added in separate steps or in any combination and in any order. As heterocoagulation progresses, large visible aggregates may begin to form. Addition of one or more polymeric dispersants can disperse the particles having an MRL external coating. The dispersant allows such particles to stay or return to a state of colloidal suspension. The dispersant is preferably added to the process in the range of 0° to 100° C.

In some instance, flocculation can occur between the MRM of the external MRL of one particle with the MRM of the external MRL of another particle. As such, the MRL coated particles can agglutinate together by flocculation, which is adverse to the desire of obtaining mutually distinct MRPs that have limited interactions with each other. Such unfavorable flocculation can be avoided or counteracted by using a dispersant. The dispersant can be used in an amount that inhibits flocculation and can keep individual MRPs from adversely interacting with each other.

After a particle includes at least one MRL so as to be an MRP, the external MRP comprised of MRMs can be encapsulated within a polymeric layer or coating. The interior polymeric layers and/or exterior polymeric coating can be useful for increasing the shelf-life and overall stability of the MRP. For example, a particle characterized as having a core/MRM/dispersant (optionally containing a heterocoagulant) can be over-coated with a polymeric material to provide such increased shelf-life and stability.

The polymeric layer or polymeric coating can be prepared by any number of methods including the following exemplary techniques: direct application of a polymeric coating (e.g., such as styrene, methacrylates, and the like); application of monomers and a polymerization initiator under conditions suitable for polymerization; cross-linking carboxylic acid groups present in the dispersant; neutralizing an acidic polymeric dispersant (e.g., polymethylacrylic acid) with a basic monomer (e.g., N-vinylcarbazole or dimethylaminoethyl methylmethacrylate) and then polymerizing with styrene; and combinations thereof.

For example, the heterocoagulation of MRM on core particles can be facilitated with PEI as a dispersant. The PEI can be cross-linked with itself using cross-linkers such as ethylene dibromide, ethylenedichloride, gluteraldehyde, formaldehyde, N',N-methylenebisacrylamide, methylenebisepoxide, or the like. The cross-linked PEI can then be over-coated with a polymeric layer with polyacrylic acid, polymethacrylic acid, or a mixture thereof. Following the polymeric over-coating, PEI can be cross-linked with the polyacrylic acid and/or polymethacrylic acid of the polymeric layer using one or more of 1-ethyl-2-(3-dimethylaminopropyl) carbodiimide (EDAC), N',N'-dicyclohexylcarbodiimide, ethylchloroformate, or the like.

Moreover, the first MRL can be deposited onto the core by mainly Van der Waals forces, and held thereto by use of a dispersant and/or polymeric overcoat. After the first coating of the MRM and polymeric layer, the excess ferrofluids can be washed away so that the MRMs are encapsulated between the core and polymeric overcoat. As such, the amount of MRM in the first MRL can be limited by the amount of agglutination and the ability of the cross-linked dispersant and/or polymer to hold the MRM to the underlying core.

In view of the foregoing, the amount of MRM agglutinated onto the core or any polymeric layer may be controlled such that the MRM in the first layer, second layer, and/or any number of MRLs can comprise about 0.1% to about 80% of the total weight of the finished MRP, preferably about 5% to about 50%, and most preferably from about 10% to about 40% of the total weight of the finished MRP.

After being coated, the particles characterized as having a core/MRM/polymer configuration (with or without optional heterocoagulant and/or dispersant) can be further reacted with more MRM to form another MRL over the polymeric coating, which then becomes an interior polymeric layer. Since the polymeric layer and MRM have opposing charges, the second MRM having the MRM can form via ionically-driven heterocoagulation. Again, the amount of MRM coated onto the core or interior polymeric layers may be controlled such that the MRM in any of the MRLs includes a sizable percentage of the total weight of the finished particle.

Optionally, the most external MRL can then be exposed to the dispersant as before. The dispersed MRP comprising two or more MRLs can be optionally coated with a polymeric coating as described above. The sequential steps of heterocoagulation, optional dispersal, and polymeric coating may be repeated as necessary in order to provide a MRP having the proper magnetically responsiveness, residual magnetism, size, drag, sedimentation properties, and the like.

Additionally, various outer coating strategies can be used to address the problem of encapsulating a hydrophilic amphoteric core surface surrounded by a hydrophilic protective colloid with uncharged hydrophobic monomers. Unsatisfactory over-coating can result in MRPs that may fall apart upon exposure to acid or base solutions, which makes the net charge on the magnetite reverse. As such, the overall sizes of the MRPs can include the outer polymeric coating to aid in increasing long-term stability, reusability, and shelf-life.

Moreover, the second and other MRLs can be deposited onto the underlying polymeric layer by mainly electrostatic interactions; however, some amount of Van der Waals forces attribute to the agglutination of MRM to the polymer. Also, the MRL can be held to the underlying polymeric layer by the electrostatic interaction, and the stability can be increased by the use of the heterocoagulants, binder, and/or dispersant, which can be cross-linked to encapsulate the MRL. Also, each MRL can be held to the underlying polymer layer with a polymeric overcoat that has a significant amount of acid layers. As such, electrostatic forces can be used to hold the MRL to each polymeric layer. After each coating of the MRM and polymeric layer, the excess ferrofluids can be emulsified and re-suspended for the next polymerization process. Thus, a significantly increased amount of MRM can be immobilized on to each polymeric layer.

Additionally, the external polymeric coating of a MRP can be prepared to include a variety of functional moieties. As such, the carboxylic groups on the external polymeric coating can be activated with well-known activators, such as DCC, EDAC, and the like, in order to facilitate coupling with amine groups that are present on the functional moieties. It is common for functional moieties, such as antibodies, antibody fragments, antigens, haptens, ligands, receptors, and the like, to include amine groups that can react with an activated carboxylic group. However, it should be recognized that various other techniques can be used to couple a functional moiety to an external polymeric coating of a MRP.

IV. Improvements and Uses of Magnetically Responsive Particles

In a preferred embodiment of the present invention, the MRPs disclosed herein can be produced easily and economically. It was believed that the benefits of increasing the amount of MRM in a MRP may be lost to the corresponding increase in particle size, particle surface area, weight, excess residual magnetism, and the like that are likely to occur by adding additional layers of MRM and polymeric materials. Also, instability of larger particles was thought to preclude the ability to prepare MRPs with multiple MRLs and polymeric layers. Also, adding too much MRM in a single MRL can lead to particle instability. Because of these and other problems, traditional MRPs have been included to have minimal amounts of MRM, and only one MRL and one polymeric coating. However, the present MRP having multiple MRLs and multiple polymeric layers has been prepared to have faster magnetic response times and equal or greater stability compared to previous particles having only one MRL (see, U.S. Pat. No. 5,648,124).

Accordingly, it has been found that the addition of multiple MRLs and polymeric layers can produce a marked improvement in response time relative to other magnetic particles presently available. Additionally, the multiple MRLs, each encapsulated with polymeric layers and coating, can drastically increase the stability, reusability, longevity, lack of residual magnetism, and shelf-life of the MRPs of the present invention. Also, it has been found that the MRPs having multiple MRLs can have half the response time compared to prior MRPs having a single MRL. That is, the MRPs having multiple MRLs respond to a magnetic field twice as fast as prior MRPs having a single MRL, drastically improving the precision and accuracy of assays, such as immunoassays. Thus, the MRPs having multiple MRLs can have magnetic response times that are at least about 25% faster, more preferably at least about 50% faster, even more Preferably at least about 75% faster, and most preferably at least about 100% faster (e.g., two-times faster) than particles having only one MRL.

Without being bound or limited to any particular theory, it is believed that the process of the present invention, since it relies upon heterocoagulation, guarantees that the magnetic dipoles of the aggregates of magnetite remain unaligned as they are absorbed randomly onto the surface of the core particle, even at high magnetite loadings. Accordingly, the MRPs prepared according to the present invention can exhibit negligible residual magnetism having magnetic squareness of less than 0.1 and remain in suspension for long periods of time. The magnetic squareness of the invention microparticles can vary between 0 to 0.1. The magnetic squareness can be defined as rententivity divided by magnetism. Squareness is a measure of the residual magnetism left in the microparticles after being exposed to a magnetic field. A magnetic squareness of 0.1 indicates that 10% of the induced magnetism remains, and a magnetic squareness of 0.02 indicates that only 2% of the induced magnetism remains.

Additionally, the MRPs in accordance with the present invention can be characterized by their behavior when suspended in water. In particular, MRPs can be colloidally stable in water, and exhibit zero to negligible residual magnetism after being exposed to a magnetic field. The term colloidally stable can refer to particles that when dispersed in water at concentrations from 0.1 to 10 grams per 100 milliliter may be seen to be in Brownian motion, fully dispersed, and not clumped together. This can be observed when a 10 microliter sample of the MRP dispersion under a cover slip is examined at 400× magnification using an inverted light microscope. The MRPs may also be sized by quasielastic light scattering ("QELS"). However, it should be noted that particles that are not colloidally stable usually can not be sized by QELS.

Accordingly, colloidally stable MRPs can be dispersed in water at a total solids loading of 0.1 to 10 grams per 100 milliliter, and show limited settling after approximately one week of sitting undisturbed at room temperature. The settling amount can be measured by determining the portion of the total volume, which is clear and does not contain dispersed. MRPs after initial dispersion in 100% of the total volume.

Moreover, the MRPs can also have negligible magnetic hysteresis, where negligible includes no hysteresis. Magnetic hysteresis can be observed from the measurement of residual magnetism in an MRP once it has been exposed to a magnetic field and the magnetic field has been pulled away or terminated. Having negligible to no hysteresis and/or the magnetic squareness values mentioned above can be easily re-dispersed by gentle stirring, vortexing, shaking, or the like. MRPs that exhibit negligible hysteresis typically have magnetic squareness values of less than or about 0.1. The preferred range of magnetic squareness is 0 to 0.05.

As described above, the MRPs may be used in a variety of experimental procedures. One particularly important experimental procedure can include immunoassays where an antigen or antibody is bound to the polymeric coating on the MRP. Such bonding may be accomplished by physical adsorption or by covalent chemical bonding with well-known linker and/or linking reagents (e.g., carboduimide). Such antigen/antibody functionalization is known in the art and described in, e.g., E.P. 420,186, incorporated herein by reference. For example, streptavadin has been coupled to MRPs produced according to the above-described process and the activity of the bound streptavadin was confirmed using a functional assay.

Previous particles that are responsive to magnetic fields had magnetic responsiveness that was only suitable for use in automated assays and associated equipment. It has now been found that the MRPs having multiple MRLs can be used in manual assays that are performed with handheld equipment. In part, the MRPs having multiple MRLs can have about half the response time compared to prior MRPs having a single MRL. It is thought that the halved response time can contribute to the use in manual assays, which are less sophisticated and controllable compared to automated assays.

Additionally, it has been found that the MRPs having multiple MRLs have improved sedimentation characteristics in a gravitational field. When an MRP is suspended in solution and subjected to a gravitational field, three forces act on the particle. First, there is the sedimenting or gravitational force, Fs, which is proportional to the mass of the MRP and the acceleration provided by gravity. Second, there is a buoyant force, Fb, that is equal to the weight of the fluid under Archimedes' principles. Third, a frictional drag, Fd, which is proportional to the velocity, but also depends on the shape and size of the particle. Bulky particles can experience comparatively more drag.

In view of the foregoing, it was unexpected that the MRPs having multiple MRLs can increase the ability to be retained in suspension in an aqueous solution. That is, the size, shape, surface characteristics, and density of the MRP can improve the suspension in solution such that less agitation is required to maintain suspension. Accordingly, less agitation can be used during the assay, which makes the assay less complicated and reduces unwanted consequences arising from agitating samples. For example, increased agitation can cause the MRPs in solution to come into contact with each other, other particles, and the walls of the container with increased forces. Such increased forces can decrease stability, longevity, and shelf-life between uses. Thus, the MRPs having multiple MRLs can have longer stability, longevity, and shelf-life between uses due to being used in a less agitated environment. Moreover, less agitation can be beneficial for the other components used within the assay, such as cells, which can be destroyed by over-agitating.

Additionally, the ability to retain suspension in solution can increase the ability of the MRPs having multiple MRLs to be re-suspended after being first suspended. That is, the MRPs can stay suspended longer while on the shelf so that less agitation is required for re-suspension. Accordingly, some assays that require a dormant, non-agitated incubation can be improved because less agitation is required to maintain suspension and/or to fully re-suspend the MRPs.

Moreover, it has been found that the characteristics of the MRPs having multiple MRLs that improve the ability to stay suspended or be rapidly re-suspended do not negatively impact the magnetic response times. Accordingly, even though the particles have favorable properties that may be attributed to increased drag, the MRPs having multiple MRLs have improved response times over prior particles having a single MRL. Also, the MRPs having multiple MRLs have nearly double the response speed compared to particles having a single MRL. Thus, the MRPs having multiple MRLs are functionally about twice as fast as particles having a single MRL.

The increase in magnetic responsiveness can even be obtained in biological matrices that are thicker than standard solutions. As such, when a sample contains blood, cell lysate, and the like, the sample is usually thicker than a standard solution. However, the MRPs having multiple MRLs can still have improved response times in such thicker samples.

The drag experienced by an object moving through a fluid is described by the following equation: $D=1/2\rho v^2 AC_d$ where D is the force of drag; $\rho$ is the density of the fluid; v the velocity of the object moving through the fluid; A is a function of the surface area of the object; and $C_d$ is the drag coefficient of the object. The drag can be compared between MRPs having multiple MRLs and particles having a single MRL. Since two similar objects are moving through a similar fluid, the equation can be simplified such that most of the variables factor out. $C_d$ probably will not factor out completely because $C_d$ for a spherical object is dependent on the sphere's diameter and the velocity of the sphere relative to the fluid. However, because the changes in diameter are relatively small and the velocities are quite low, the differences in Cd should be negligible. Thus the drag experienced by the two particle types is approximately equal to the square of the velocity times the surface area of the particles, or in mathematical notation, $D \approx v^2 A$. From this equation it naturally follows that in order to, for example, double the velocity of a particle moving through the fluid a quadrupling of the force applied to the particle may be required. One way that the magnetic force exerted on a particle can be increased is to apply additional layers of MRM and polymer coating. However, this would tend to increase the surface area of the particle, which would also tend to increase the drag experienced by the particle.

Based on this theoretical foundation, it is unexpected that simply adding additional layers of MRM and polymer coating can drastically improve magnetic response times. That is, it is surprising that enough additional MRM can be added to increase the magnetic response time without also increasing the surface area and/or diameter to such a degree that the advantage of the additional magnetic attraction was lost. Given that theoretical foundation, the observed improvement in response time, which is shown in the following examples, was quite unexpected and surprising.

EXAMPLES

The following examples are provided to illustrate embodiments of the prevention and are not intended to be limiting. Accordingly, some of the examples have been performed via experiment and some are prophetic based on techniques, standards, and results well known in the art. Also, it should be apparent that the invention can include additional embodiments not illustrated by example. Additionally, many of the examples have been performed with experimental protocols well known in the art using the MRPs prepared in accordance with the present invention. Moreover, the experimental protocols of U.S. Pat. No. 5,648,124 are useful for preparing aspects of the present invention, and are incorporated herein by reference.

Example 1

Approximately 549.0 grams ("g") of 5.2% ferrofluid (e.g., 28.5 g solids), prepared according to U.S. Pat. No. 5,648,124, and about 192.0 g of 10% ion-exchanged cleaned 0.8 micron carboxylate modified polystyrene microparticles (e.g., 20.0 g solids) are added to a blender and mixed at low speed for approximately one minute. About 200 milliliters ("mL") of 2 molar ("M") NaCl is added at a rate of about 180 mL/min while blending. The mixture is blended at low speed for another minute after the complete addition of NaCl, and then 100 mL of 0.22 mcm filtered 10% (w/w) PEI (e.g., average M.W. 50,000-60,000) is added at the rate of about 180 mL/min with continuous blending. The mixture is blended for an additional minute at low speed, whereupon the mixture is magnetically decanted and re-suspended in 1 L of 0.25 M NaCl. The steps of magnetically decanting and re-suspension in NaCl are repeated three more times.

The PEI coated microparticles are added to the blender once again and blended for about one minute at low speed. Then, approximately 100 mL of 10% polymethacrylic acid resin (PMAA, average M.W. 5000-15000) is added at the rate of about 180 mL/min with continuous blending. The mixture is blended for another minute and then magnetically decanted and re-suspended in 1 L of 0.25 M NaCl, which is repeated twice for a total of three cycles of decanting and re-suspension. The mixture is then magnetically decanted and re-suspended in 1L of 50 mM MES buffer at pH 5.9, and stirred for about 30 minutes.

The polymers are then cross-linked by adding about 25 g of EDAC in 100 mL of deionized water to the above mixture. After approximately 16 hours of cross-linking, the particles are washed 2-6 times with deionized water.

The resulting MRP were measured by QELS; which determined a diameter of about 0.8 micron. The surface charge density was measured by conductometric titration, which determined a surface charge density from about 0.49 meq/g to about 0.67 meq/g. Also, the particles were brown in color. The percent solids were determined to be from about 4.8% solids to about 5.2% solids.

Example 2

Approximately 400 g (e.g., 5% solids) of the resulting MGCM microparticles from Example 1 and about 549 g of 5.2% ferrofluid (e.g., 28.5 g solids) are added to a blender and mixed at low speed for approximately one minute. About 200 mL of 2 M NaCl is added at a rate of about 180 mL/min while blending. The mixture is blended at low speed for another minute after the complete addition of NaCl, and then 100 mL of 0.22 micron filtered 10% (w/w) PEI (e.g., average M.W. 50,000-60,000) is added at the rate of about 180 mL/min with continuous blending. The mixture is blended for an additional minute at low speed, whereupon the mixture is magnetically decanted and re-suspended in 1 L of 0.25 M NaCl. The steps of magnetically decanting and re-suspension in NaCl are repeated three more times.

The microparticles are returned to the blender and blended for about one minute at low speed. Then, approximately 100 mL of 10% PMAA is added at the rate of about 180 mL/min with continuous blending. The mixture is blended for another minute and then magnetically decanted and re-suspended in 1 L of 0.25 M NaCl, which is repeated twice for a total of three cycles of decanting and re-suspension. The mixture is then magnetically decanted and re-suspended in 1 L of 50 mM MES buffer at pH 5.9, and stirred for about 30 minutes.

Cross-linking is accomplished by adding 25 g of EDAC in 100 mL of deionized water to the above mixture. After approximately 16 hours of cross-linking, the particles are washed 2-6 times with deionized water.

The yield is about 1000 g at about 5% solids. The diameter by quasi-elastic light scattering is approximately 1.3 micron with a polydispersity factor, $\mu^2/\mu^2$, of 0.30. The surface charge density was measured by conductometric titration, which determined a surface charge density from about 0.40 meq/g to about 0.58 meq/g. Also, the particles were brown in color. The percent solids were determined to be from about 4.8% solids to about 5.2% solids.

Example 3

Magnetic response time tests are used to evaluate the MRPs comprising two or more MRLs, produced according to Example 1, versus the microparticles comprising a single layer of MRM, produced according to methods described in Example 15 of U.S. Pat. No. 5,648,124. Accordingly, particles having multiple MRLs are designated as MRPs, and those with a single layer are designated as '124 particles.

To perform the response time test, a 0.05% solids suspension is prepared for each type of the microparticles, and the suspension is added to a spectrophotometer cell. Absorbance at 600 nm is monitored while the suspension is exposed to a magnet mounted on one side of the cell. The response time is measured as the number of seconds required for the absorbance to be reduced by 95% of the absorbance value at time-zero. The results are as follows: magnetic response time for '124 particles with single MRM layer are about 109 seconds; and magnetic response time for MRPs with two MRM layers are about 47 seconds.

Example 4

An exemplary MRP having multiple MRLs is characterized as follows: the diameter of the core is about 0.85 micron; the diameter of the core/MRL is about 1 micron; the diameter of the core/MRL/polymer/MRL/polymer is about 1.2 to about 1.5 micron; and the thickness of a single MRL is about 0.2 micron.

Example 5

The MRPs having multiple MRLs can be provided with an antibody to determine the amount of total binding for a corresponding analyte of interest, wherein the antibody is an antibody against the antigen and the antigen is the analyte of interest (analyte can be a different antibody, such as antibody against HIV; analyte can be a peptide or protein; analyte can be synthetic molecule or carrier protein containing small molecule or peptides) As such, the MRPs having an antibody can be used in a heterogeneous microparticle immunoassay. This assay can be either manual or automated format in various platforms such as slide agglutination. This assay can measure the hormone level in human serum or plasma. The assay can be performed by combining a sample containing the analyte, assay diluent (e.g., a buffer), an antibody coated MPR, and free antibody are combined. The analyte present in the sample binds to the antibody coated microparticles and the free antibody. After an incubation period, a competing antigen is added to the reaction mixture, and it binds to the free analyte or the antibody bound to the MPR. After washing to remove free competing antigen and competing antigen/antibody complex, the competing antigen and antibody coated MPR complex can generate signal (which is dependent on which detection system is used).

Figure 5:
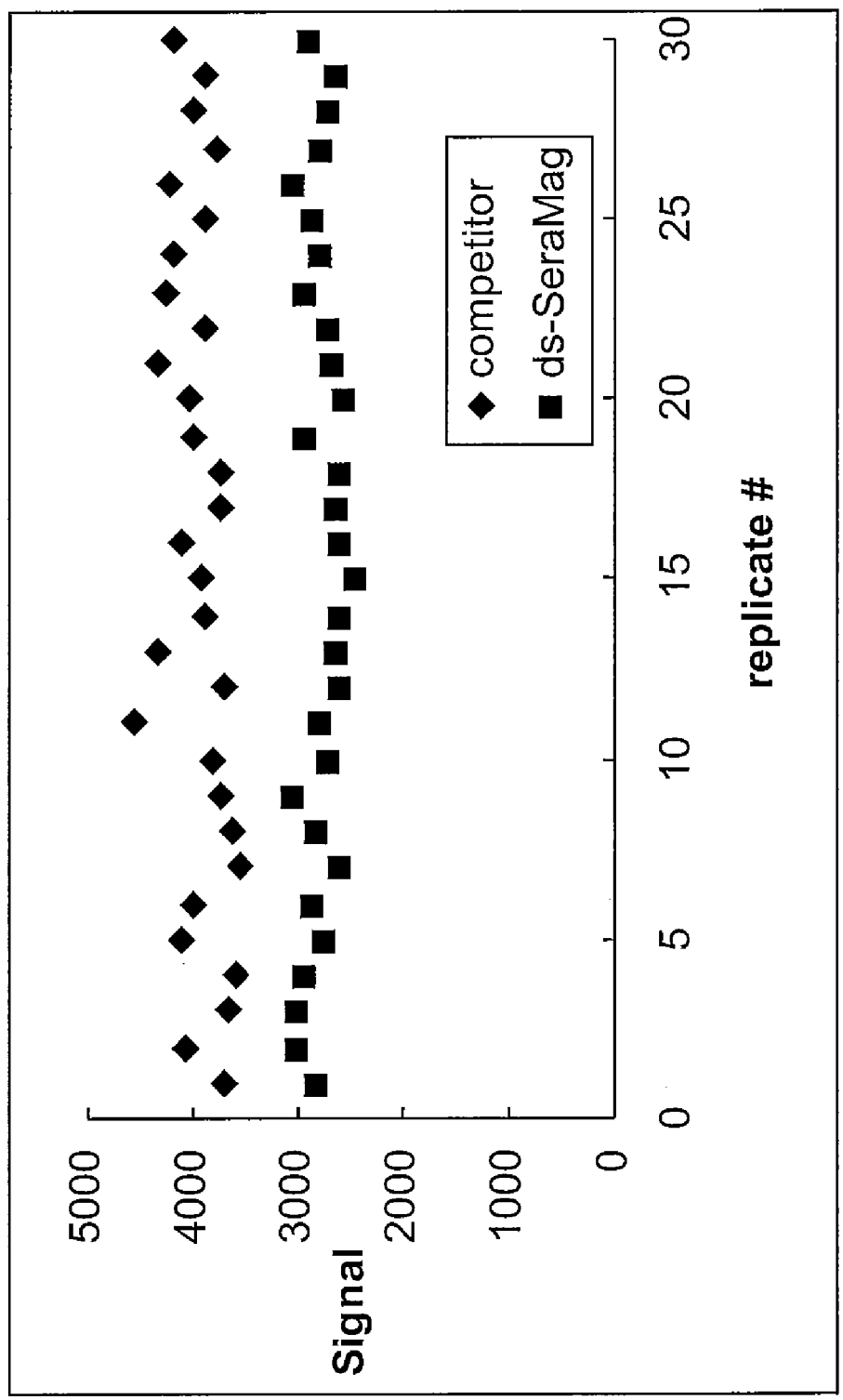
FIGS. 5-7 are graphs illustrating the ability of an MRP having multiple layers to function in an immunoassay.

The foregoing Heterogeneous Immunoassay protocol was followed using the MRPs of the present invention compared to commercially available magnetic microparticles ("commercial particle"). FIG. 5 illustrates the results of the foregoing Heterogeneous Immunoassay using the MRP (e.g., ds-SeraMag) and commercial particle with plain serum without any analyte. As such, FIG. 5 is a background reading of the signal and it reflects the non-specific binding ("NSB") of the particles. As shown, the NSB for the MRP having multiple MRLs is lower than the NSB for the commercial particles. The NSB is a very important characteristic of the particle in the application. The NSB is closely related to such factors as noise-to-signal ratio, false results, and precision of the application. The lower the NSB, the better the particle performs. For example, both particles have signal 12000. But the one with lower NSB shows background noise signal 3000, compared to the one with higher NSB with 400 background, thus giving significantly better ratio of signal-to-noise.

Figure 6:
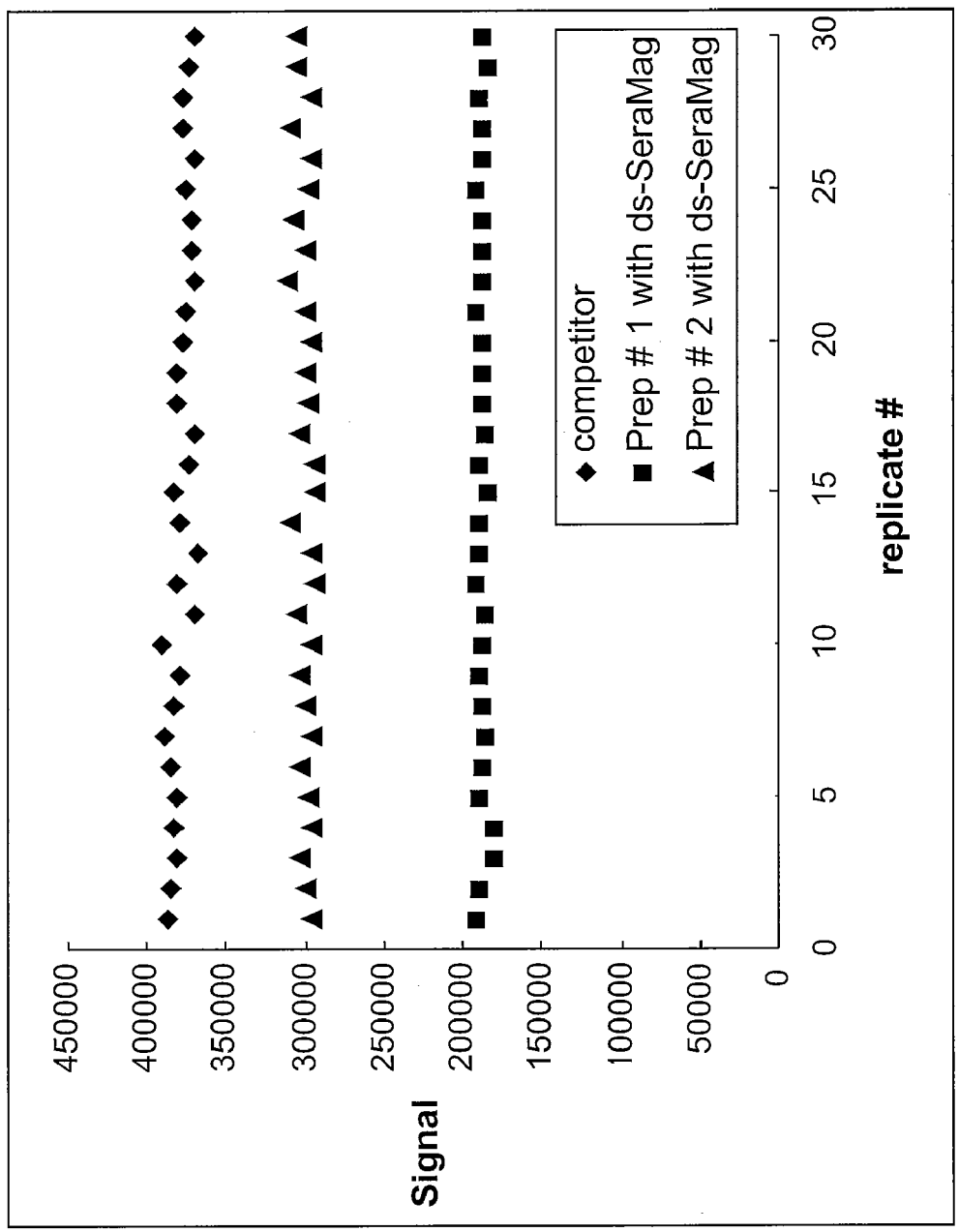

Additionally, the foregoing Heterogeneous Immunoassay protocol was followed using the two different MRPs having multiple MRLs (e.g., Prep #1 with ds-SeraMAg and Prep #2 with dsSeraMag at a different condition of antibody coupling) prepared in accordance with the present invention compared to the commercial particle. FIG. 6 illustrates the results of the foregoing Heterogeneous Immunoassay using the MRP and commercial particle with 5 mg/dL analyte concentration. As such, FIG. 6 shows that at the concentration of 5 mg/dL, as shown by the signal/analyte/noise, the MRPs have low background and good signal reproducibility. Also, FIG. 6 shows the coefficient of variance ("CV") of the MRPs are less than 2.5%. One important aspect of the application is precision of the results. The most critical factor that determines the precision is the magnetic response time of the particles. In the application, the magnet separation force and separation time do not change. A slower response will not be efficient enough to separate all particles from solution in the allotted time. So the washing step (after the separation step) will also wash away particles. This will cause loss of precision in the application. In this case, the response time determines whether the particles will be useful or not. Both FIGS. 5 and 6 show the particles have very good precision.

Figure 7:
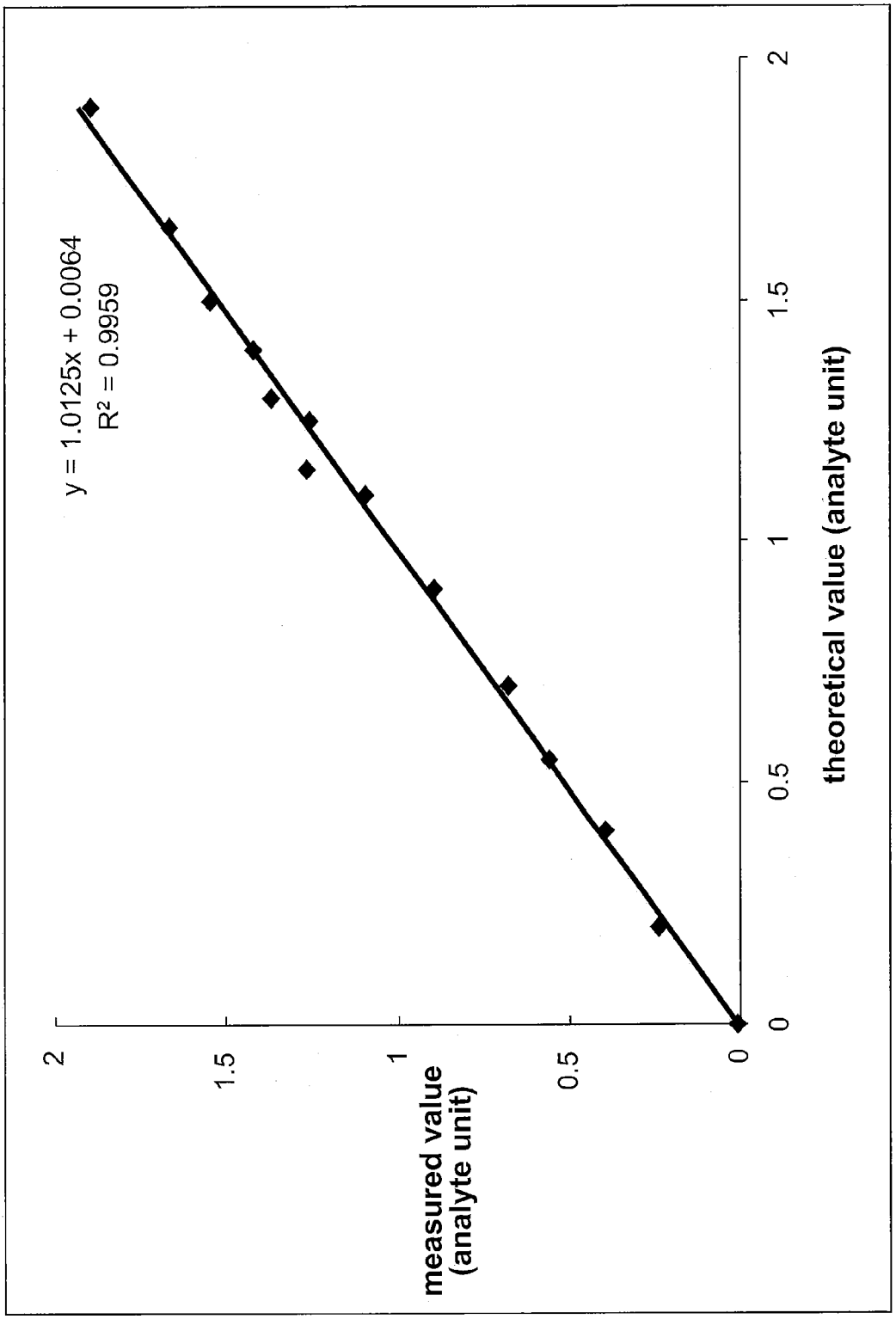

FIG. 7 is a graph illustrating that the MRPs can provide measured values substantially equivalent to theoretical values. As such, the measured analyte units for different concentrations of analyte can be compared to theoretical analyte units. The linearity of FIG. 7 indicates that the MRPs of the present invention have significant accuracy and quality. In part, this is shown by the linearity as the concentration of analyte increases and $R^2$ being greater than about 0.995. FIG. 7 shows that good results are obtained from a combination of low NSB and good precision. The high $R^2$ value shows high precision. The slope is close to 1 and this means a low bias. The low background signal noise makes the intercept close to 0.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:
1. A magnetically responsive particle having substantially no residual magnetism and an improved magnetic response time, comprising:
   an electrically charged core layer;
   a first magnetically responsive layer on the core layer, said first magnetically responsive layer comprising a ferrofluid that includes a plurality of magnetically responsive grains, wherein each of the plurality of magnetically responsive grains in the ferrofluid has a size in a range of about 10 nm to about 120 nm, a portion of the magnetically responsive grains being agglutinated to the core layer;
   a first polymeric layer encapsulating the first magnetically responsive layer, said first polymeric layer formed by cross-linking a first monomer having a first reactive group and a second monomer having a second reactive group;
   a second magnetically responsive layer on the first polymeric layer, said second magnetically responsive layer comprising a ferrofluid that includes a plurality of magnetically responsive grains, wherein each of the plurality of magnetically responsive grains in the ferrofluid has a size in a range of about 10 nm to about 120 nm, which may be identical to or different from the ferrofluid of the first magnetically responsive layer, attached to the first or second reactive groups of the first polymeric layer; and a second polymeric layer encapsulating the second magnetically responsive layer, said second polymeric layer formed by cross-linking a third monomer having a third reactive group and a fourth monomer having a fourth reactive group, wherein the magnetically responsive particle has a magnetic response time that is at least about 50% faster as compared to a magnetically responsive particle having only one magnetically responsive layer.

2. A particle as in claim 1, further comprising at least one additional magnetically responsive layer and at least one additional polymeric layer, wherein the additional magnetically responsive layers alternate with the additional polymeric layers.

3. A particle as in claim 1, wherein at least one of the first polymeric layer or the second polymeric layer is comprised of at least one heterocoagulant that is at least one of coagulated with the magnetically responsive grains of the first magnetically responsive layer so as to facilitate binding with the core or coagulated with the magnetically responsive grains of the second magnetically responsive layer so as to facilitate binding with the first polymeric layer.

4. A particle as in claim 3, wherein the heterocoagulant includes at least one of the following:
 ammonium or alkali metal salts of sulfate and phosphate;
 free radical generating ammonium;
 alkali metal salts of peroxydisulfate, peroxydiphosphate, or 4,4-azobis(4-cyanovaleric acid);
 alkali metal salts of oxalic acid, malonic acid, succinic acid, or glutaric acid;
 polymerizable ammonium;
 alkali metal salts of fumaric acid, maleic acid, or itaconic acid;
 alkali metal salts of alkyl sulfonates;
 alkali metal salts of dihexylsulfosuccinate or dioctylsulfosuccinate;
 alkali metal salts of alpha olefin sulfonates, alkyl allyl sulfosuccinates, or allyl ether sulfonate, each having 6 to 30 carbon atoms;
 alkylamines;
 polyalkylamines;
 polyethylenimine;
 polyacrylic acid, water soluble copolymers thereof, and salts thereof;
 polymethacrylic acid, water soluble copolymers thereof, and salts thereof;
 polystyrenesulfonic acid, water soluble copolymers thereof; and salts thereof;
 polyvinylsulfonic acid, water soluble copolymers thereof, and salts thereof;
 styrene/maleic acid copolymers, half esters thereof, and salts thereof;
 vinyl methyl ether/maleic acid copolymers, half esters thereof, and salts thereof; or
 isobutylene/maleic acid copolymers, half esters thereof, and salts thereof.

5. A particle as in claim 4, wherein the heterocoagulant is a polymer having a weight average molecular weight of from about 1,000 to about 100,000 daltons.

6. A particle as in claim 1, wherein at least one of the first polymeric layer or the second polymeric layer is comprised of at least one dispersant dispersed on at least one of the first magnetically responsive layer or second magnetically responsive layer.

7. A particle as in claim 6, wherein the dispersant is at least one of:
 cross-linked together;
 cross-linked with a heterocoagulant to form a polymeric layer; or
 cross-linked together and cross-linked with the heterocoagulant to form a polymeric layer.

8. A particle as in claim 7, wherein the dispersant includes at least one of the following:
 polyacrylic acid, water soluble copolymers thereof, and salts thereof;
 polymethacrylic acid, water soluble copolymers thereof, and salts thereof;
 polystyrenesulfonic acid, water soluble copolymers thereof; and salts thereof;
 polyvinylsulfonic acid, water soluble copolymers thereof, and salts thereof;
 styrene/maleic acid copolymers, half esters thereof, and salts thereof;
 vinyl methyl ether/maleic acid copolymers, half esters thereof, and salts thereof;
 isobutylene/maleic acid copolymers, half esters thereof, and salts thereof; or
 polyethyleneimine.

9. A particle as in claim 1, wherein at least one of the first polymeric layer or second polymeric layer includes at least one of an acidic monomer, a basic monomer, a hydrophobic neutral monomer, polar monomer, or a polymer thereof.

10. A particle as in claim 1, wherein at least one of the first polymeric layer or the second polymeric layer is comprised of at least one heterocoagulant cross-linked with at least one dispersant.

11. A particle as in claim 1, wherein the magnetic response time is at least 75% faster as compared to a magnetically responsive particle having only one magnetically responsive layer.

12. A magnetically responsive particle having substantially no residual magnetism and a faster magnetic response time, comprising:
 an electrically charged core layer;
 a first magnetically responsive layer on the core layer, said first magnetically responsive layer comprising a ferrofluid that includes a plurality of magnetically responsive grains, wherein each of the plurality of magnetically responsive grains in the ferrofluid has a size in a range of about 10 nm to about 120 nm;
 a first heterocoagulant intermingled with the ferrofluid of the first magnetically responsive layer as to heterocoagulate the magnetically responsive grains on the core;
 a first dispersant covering the first magnetically responsive layer and cross-linked with the first heterocoagulant so as to form a first cross-linked polymeric layer that encapsulates the first magnetically responsive layer on the core;
 a second magnetically responsive layer bound to the first cross-linked polymeric layer, said second magnetically responsive layer comprising a ferrofluid that includes a plurality of magnetically responsive grains, which may be identical to or different from the ferrofluid of the first magnetically responsive layer, wherein each of the plurality of magnetically responsive grains in the ferrofluid has a size in a range of about 10 nm to about 120 nm;
 a second heterocoagulant intermingled with the ferrofluid of the second magnetically responsive layer so as to heterocoagulate said second magnetically responsive grains on the first cross-linked polymeric layer; and a second dispersant covering the second magnetically responsive layer and cross-linked with the second heterocoagulant so as to form a second cross-linked polymeric layer that encapsulates the second magnetically responsive layer on the first cross-linked polymeric layer, wherein the magnetically responsive particle has a magnetic response time that is at least about 50% faster as compared to a magnetically responsive particle having only the first magnetically responsive layer and the first cross-linked polymeric layer that encapsulates the first magnetically responsive layer.

13. A particle as in claim 12, wherein the magnetic response time is at least 75% faster as compared to a magnetically responsive particle having only the first magnetically responsive layer and the first cross-linked polymeric layer that encapsulates the first magnetically responsive layer.

14. A particle as in claim 12, wherein the particle has magnetic squareness of less than about 0.1.

15. A particle as in claim 14, wherein the particle has negligible residual magnetism after being exposed to a magnetic field sufficient for the particle to respond thereto.

16. A particle as in claim 12, wherein the particle is colloidally stable in water at concentrations from about 0.1 to 10 grams of particle per 100 milliliters of water.

17. A particle as in claim 12, wherein the particle has only two magnetically responsive layers.

18. A method of preparing a magnetically responsive particle having substantially no residual magnetism and a faster magnetic response time, the method comprising preparing a first aqueous dispersion comprising an electrically charged core layer and a ferrofluid that includes a plurality of magnetically responsive grains in a manner such that the magnetically responsive particles agglutinate to the core to form a first magnetically responsive layer, wherein each of the plurality of magnetically responsive grains in the ferrofluid has a size in a range of about 10 nm to about 120 nm;

adding at least one of a first dispersant or first heterocoagulant to the first magnetically responsive layer so as to form a second aqueous dispersion therewith;

encapsulating the first magnetically responsive layer with at least one of the first dispersant or first heterocoagulant so as to form a cross-linked first polymeric layer;

adding additional ferrofluid that includes a plurality of magnetically responsive grains to the first polymeric layer so as to form a second magnetically responsive layer on the first polymeric layer, wherein the magnetically responsive particles are attached to the first polymeric layer, wherein each of the plurality of magnetically responsive grains in the ferrofluid has a size in a range of about 10 nm to about 120 nm;

adding at least one of a second dispersant or second heterocoagulant to the second magnetically responsive layer so as to form a third aqueous dispersion therewith; and encapsulating the second magnetically responsive layer with at least one of the second dispersant or second heterocoagulant so as to form a cross-linked second polymeric layer, wherein the magnetically responsive particle has a magnetic response time that is at least about 50% faster as compared to a magnetically responsive particle having only the first magnetically responsive layer and the first cross-linked polymeric layer that encapsulates the first magnetically responsive layer.

19. A method as in claim 18, further comprising:

adding the first heterocoagulant to the first aqueous dispersion so as to intermingle with the ferrofluid of the first magnetically responsive layer so as to heterocoagulate the magnetically responsive grains on the core;

adding the a first dispersant so as to cover the first magnetically responsive layer and the first heterocoagulant; and cross-linking the first dispersant with the first heterocoagulant so as to form the cross-linked first polymeric layer and encapsulate the first magnetically responsive layer on the core.

20. A method as in claim 19, further comprising:

adding the second heterocoagulant to the additional ferrofluid so as to intermingle therewith and heterocoagulate the additional magnetically responsive grains on the cross-linked first polymeric layer;

adding the a second dispersant so as to cover the second magnetically responsive layer and the second heterocoagulant; and cross-linking the second dispersant with the second heterocoagulant so as to form the cross-linked second polymeric layer and encapsulate the second magnetically responsive layer on the cross-linked first polymeric layer.

21. A method as in claim 18, wherein the ferrofluid is a paramagnetic and/or a superparamagnetic material having substantially no net residual magnetism.

22. A method as in claim 18, wherein the magnetic response time is at least 75% faster as compared to a magnetically responsive particle having only the first magnetically responsive layer and the first cross-linked polymeric layer that encapsulates the first magnetically responsive layer.

* * * * *

UNITED STATES PATENT AND TRADEMARK OFFICE
CERTIFICATE OF CORRECTION

| | |
|---|---|
| PATENT NO. | : 7,989,065 B2 |
| APPLICATION NO. | : 11/436680 |
| DATED | : August 2, 2011 |
| INVENTOR(S) | : Winstead et al. |

It is certified that error appears in the above-identified patent and that said Letters Patent is hereby corrected as shown below:

Column 4
Line 27, change "stricture" to --structure--
Line 47, change "$\mu/\mu^2$" to --$\mu/\gamma^2$--

Column 7
Line 23, change "aminoethylmethacylate" to --aminoethylmethacrylate--

Column 8
Line 16, change "to a use a" to --to use a--
Line 42, change "may by accomplished" to --may be accomplished--

Column 10
Line 52, change "obtain" to --obtained--

Column 11
Lines 57-58, change "core/MRL 32 particle" to --core/MRL particle 32--

Column 13
Line 57, change "magnetically responsiveness" to --magnetic responsiveness--

Column 14
Line 64, change "even more Preferably" to --even more preferably--

Column 18
Line 52, change "$\mu^2/\mu^2$" to --$\mu^2/\gamma^2$--

Column 19
Line 31, change "peptides) As" to --peptides). As--
Line 42, change "MPR" to --MRP--

Signed and Sealed this
Twentieth Day of March, 2012

David J. Kappos
*Director of the United States Patent and Trademark Office*

CERTIFICATE OF CORRECTION (continued)
U.S. Pat. No. 7,989,065 B2

Column 23
Line 30, change "comprising" to --comprising:--

Column 24
Line 22, change "adding the a" to --adding a--
Line 34, change "adding the a" to --adding a--